US011098277B2

(12) United States Patent
Hitomi et al.

(10) Patent No.: US 11,098,277 B2
(45) Date of Patent: Aug. 24, 2021

(54) CULTURE APPARATUS AND METHOD OF CONTROLLING CULTURE APPARATUS

(71) Applicant: PHC HOLDINGS CORPORATION, Tokyo (JP)

(72) Inventors: Tsugumasa Hitomi, Gunma (JP); Tomoyoshi Tokumaru, Gunma (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 187 days.

(21) Appl. No.: 16/143,133

(22) Filed: Sep. 26, 2018

(65) Prior Publication Data

US 2019/0024036 A1    Jan. 24, 2019

Related U.S. Application Data

(63) Continuation of application No. PCT/JP2017/010678, filed on Mar. 16, 2017.

(30) Foreign Application Priority Data

Mar. 28, 2016  (JP) .............................. JP2016-063719
Mar. 28, 2016  (JP) .............................. JP2016-063720

(51) Int. Cl.
  *C12M 3/00*  (2006.01)
  *C12M 1/00*  (2006.01)
  (Continued)

(52) U.S. Cl.
  CPC .............. *C12M 41/14* (2013.01); *C12M 1/38* (2013.01); *C12M 37/00* (2013.01); *C12M 41/18* (2013.01); *C12M 41/48* (2013.01)

(58) Field of Classification Search
  CPC ........... C12M 41/14; C12M 41/18; B01L 7/00
  See application file for complete search history.

(56) References Cited

U.S. PATENT DOCUMENTS

| 6,255,103 B1* | 7/2001 | Tamaoki | ................ C12M 37/00 219/407 |
| 2003/0041572 A1* | 3/2003 | Lohr | ..................... B01D 53/02 55/385.2 |

(Continued)

FOREIGN PATENT DOCUMENTS

| JP | H5-227942 A | 9/1993 |
| JP | 2003-125754 A | 5/2003 |

(Continued)

OTHER PUBLICATIONS

Extended European Search Report issued in European Patent Application No. 17774394.5, dated Feb. 18, 2019.

(Continued)

*Primary Examiner* — Nathan A Bowers
(74) *Attorney, Agent, or Firm* — McDermott Will and Emery LLP

(57) ABSTRACT

A culture apparatus including: a heat-insulated casing including an inner case surrounding a culture space, and an outer case, the heat-insulated casing having an opening; a box-shaped heat-insulated door to open and close the opening; and, one or more heaters provided to one or more inner surfaces of the inner case and an inner surface of an inner wall surface of the heat-insulated door, the inner wall surface facing the culture space when the door is closed; the heaters including one or more first heaters turned on when the interior of the culture space is at a first temperature to incubate a culture in the culture space and when the interior of the culture space is controlled at a second temperature to make the interior of the culture space, and second heaters to be energized when the interior of the culture space is controlled at the second temperature to sterilize the interior of the culture space.

6 Claims, 14 Drawing Sheets

(51) Int. Cl.
*C12M 1/38* (2006.01)
*C12M 1/12* (2006.01)
*C12M 1/02* (2006.01)
*C12M 1/36* (2006.01)

(56) References Cited

U.S. PATENT DOCUMENTS

| | | | |
|---|---|---|---|
| 2012/0083030 A1* | 4/2012 | Busujima | C12M 37/00 435/303.1 |
| 2013/0089924 A1 | 4/2013 | Yamasaki et al. | |
| 2014/0120610 A1 | 5/2014 | Yamashita et al. | |
| 2014/0311025 A1* | 10/2014 | Pauls | A01G 9/24 47/17 |
| 2014/0331707 A1* | 11/2014 | Yamasaki | F28D 15/02 62/291 |
| 2015/0050725 A1* | 2/2015 | Pieczarek | C12M 29/26 435/303.1 |
| 2015/0204601 A1* | 7/2015 | Baker | C12M 41/14 62/440 |

FOREIGN PATENT DOCUMENTS

| | | |
|---|---|---|
| JP | 2010-154792 A | 7/2010 |
| JP | 2013-066436 A | 4/2013 |
| KR | 10-2012-0005886 A | 1/2012 |
| WO | 2012/173076 A2 | 12/2012 |
| WO | 2016/158337 A1 | 10/2016 |

OTHER PUBLICATIONS

International Search Report issued in International Patent Application No. PCT/JP2017/010678, dated May 23, 2017; with English translation.
Written Opinion of the International Searching Agency issued in International Patent Application No. PCT/JP2017/010678, dated May 23, 2017; with English translation.
Notice of Reasons for Refusal issued in corresponding Japanese Patent Application No. 2018-509019, printed Oct. 24, 2019; with English translation.
Communication of a Notice of Opposition dated Oct. 12, 2020, issued in counterpart European Patent Application No. 17774394.5.
Brief Communication dated Dec. 21, 2020, issued in counterpart European Patent Application No. 17774394.5.
Communication of Notices of Opposition (R. 79(1) EPC) dated Dec. 23, 2020 issued in counterpart European Patent Application No. 17774394.5.

* cited by examiner

| | CUTURE MODE | STERILIZATION MODE |
|---|---|---|
| CULTURE HEATER | ON (DUTY CONTROL) | ON (DUTY CONTROL) |
| STERILIZATION HEATER | OFF | ON |

|  | OFF | CUTURE MODE | STERILIZATION MODE |
| --- | --- | --- | --- |
| CULTURE HEATER | OFF | ON (DUTY CONTROL) | ON (DUTY CONTROL) |
| STERILIZATION HEATER | OFF | OFF | ON |
| HEATER POWER CONSUMPTION | 0 [W] | 360 [W] | 720 [W] |

FIG. 11

|  | OFF | CUTURE MODE | STERILIZATION MODE |
|---|---|---|---|
| HEATER | OFF | ON (DUTY CONTROL) | ON (DUTY CONTROL) |
| HEATER POWER CONSUMPTION | 0 [W] | 720 [W] | 720 [W] |

FIG. 14

(A) ONE IN STERILIZATION MODE
ONE IN CULTURE MODE (B) TWO IN CULTURE MODE

CULTURE APPARATUS AND METHOD OF CONTROLLING CULTURE APPARATUS

CROSS-REFERENCE TO RELATED APPLICATION

The present application is a Continuation of International Patent Application No. PCT/JP2017/010678, filed on Mar. 16, 2017, which in turn, claims priority from Japanese patent application numbers 2016-063719 and 2016-063720, both filed on Mar. 28, 2016, the entire disclosure of which applications are hereby incorporated by reference herein.

TECHNICAL FIELD

The present disclosure relates to a culture apparatus and a method of controlling the culture apparatus.

BACKGROUND ART

There have been developed culture apparatuses for incubating a culture of cells, microorganisms or the like in the culture spaces thereof. For example, a culture apparatus has been developed which includes a bottom heater for heating water in a humidification pan in its culture space and a heater for heating the culture space, and in which temperature and humidity in the culture space are appropriately controlled by controlling these heaters individually (Japanese Patent Application Publication No. H5-227942).

Further, a culture apparatus capable of making its culture space sterile using such heaters is known.

SUMMARY OF INVENTION

However, in order to make the culture space sterile by heating, a heater with a large capacity generating a large amount of heat must be employed because the interior should be heated to a temperature higher than a temperature in incubating a culture.

Thus, the rate of temperature rise is fast when the heater is turned on. As a result, it becomes difficult to control temperature when incubating a culture. Further, running and stopping a larger current may also cause an increase in electromagnetic noise.

The present disclosure has been made in view of such an issue as described above, and an object thereof is to make it possible to efficiently control a culture apparatus in which a culture space can be made sterile by heating.

A culture apparatus according to an embodiment of the present disclosure includes: a heat-insulated casing including an inner case surrounding a culture space, and an outer case surrounding the inner case, the heat-insulated casing having an opening in its front surface; a box-shaped heat-insulated door to open and close the opening of the heat-insulated casing; one or more heaters provided to one or more inner surfaces of the inner case and an inner surface of an inner wall surface of the heat-insulated door, to heat an interior of a culture space, the inner wall surface facing the opening when the door is closed; and a control unit configured to turn on the heaters, the heaters including one or more first heaters and one or more second heaters, the first heaters configured to be turned on, when the culture space is controlled at a first temperature to incubate a culture in the culture space, and when the culture space is controlled at a second temperature to sterilize the culture space, the second temperature being higher than the first temperature, and the second heaters configured to be turned on, when the culture space is controlled at the second temperature to sterilize the interior of the culture space.

BRIEF DESCRIPTION OF THE DRAWINGS

FIG. 11 is a diagram to explain a control mode of a heater according to an embodiment of the present disclosure.

FIG. 14 is a diagram to explain a control mode of a heater according to another embodiment.

DETAILED DESCRIPTION OF EMBODIMENTS

A culture apparatus 1 according to an embodiment of the present disclosure will be described with reference to drawings. The culture apparatus 1 is an apparatus in which cultures such as cells and microorganisms are incubated.

First Embodiment

Figure 1:
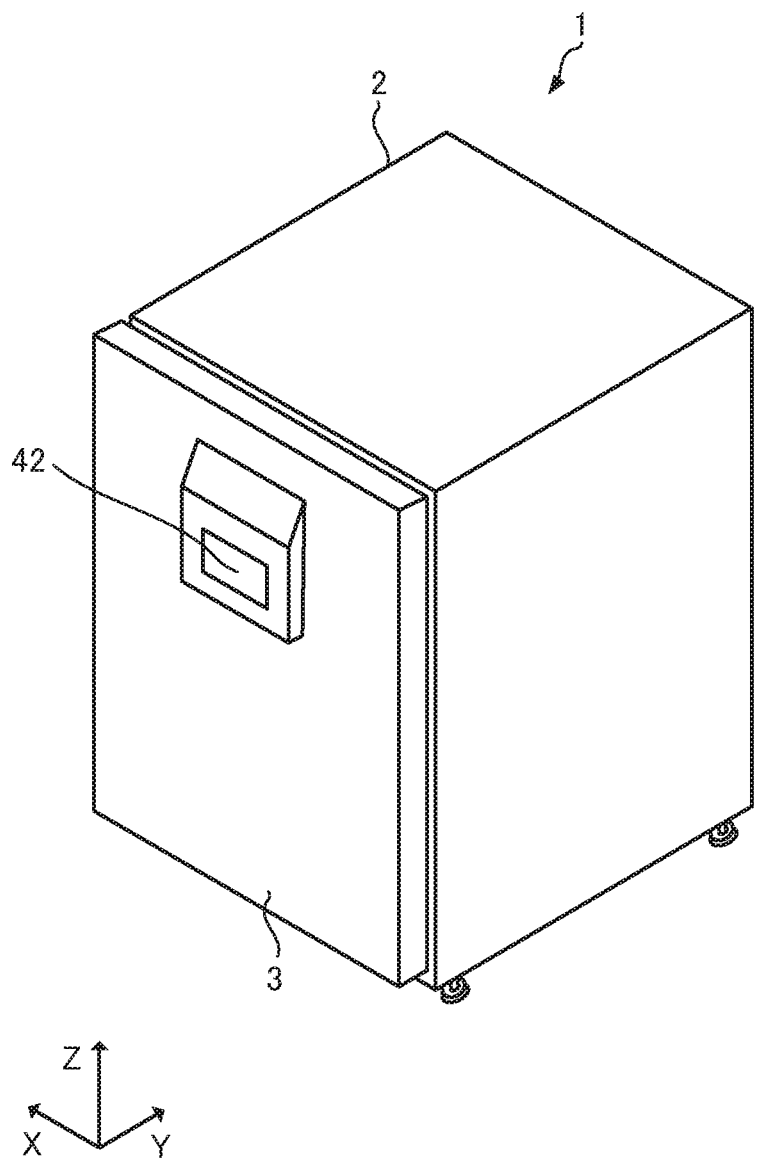
FIG. 1 is an external perspective view of a culture apparatus according to an embodiment of the present disclosure.
Figure 2:
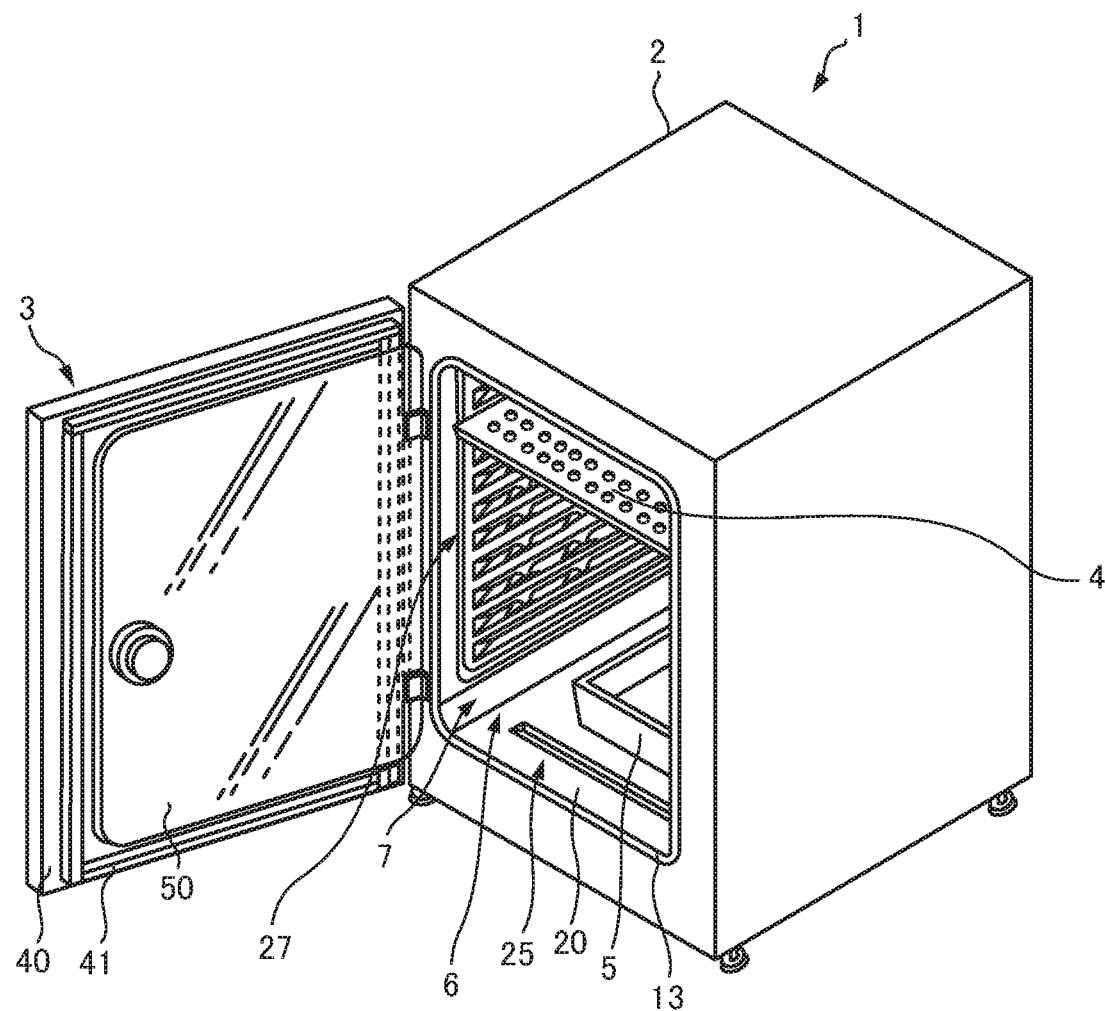
FIG. 2 is an external perspective view of a culture apparatus according to an embodiment of the present disclosure.
Figure 3:
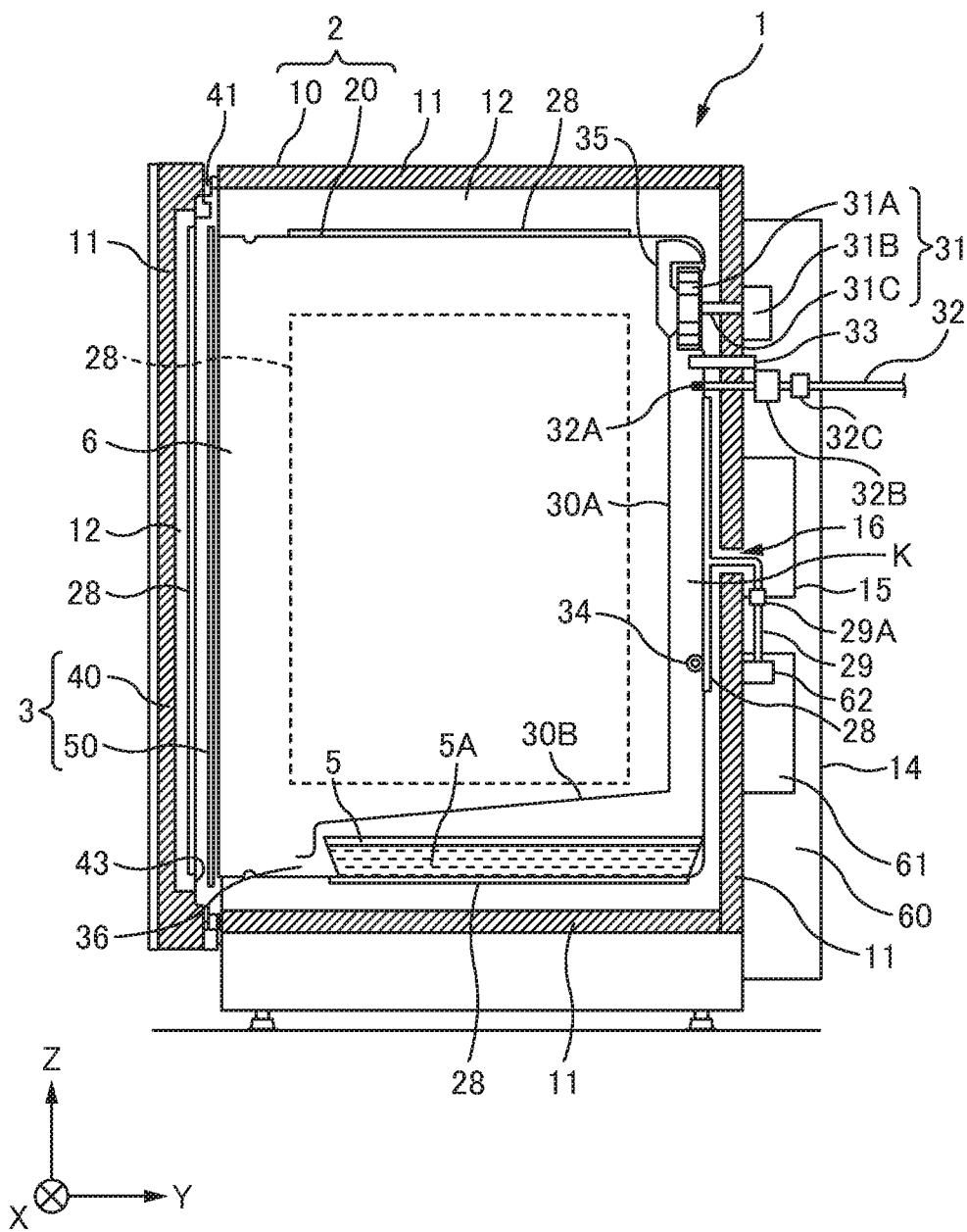
FIG. 3 is a cross-sectional view of a culture apparatus according to an embodiment of the present disclosure.
Figure 4:
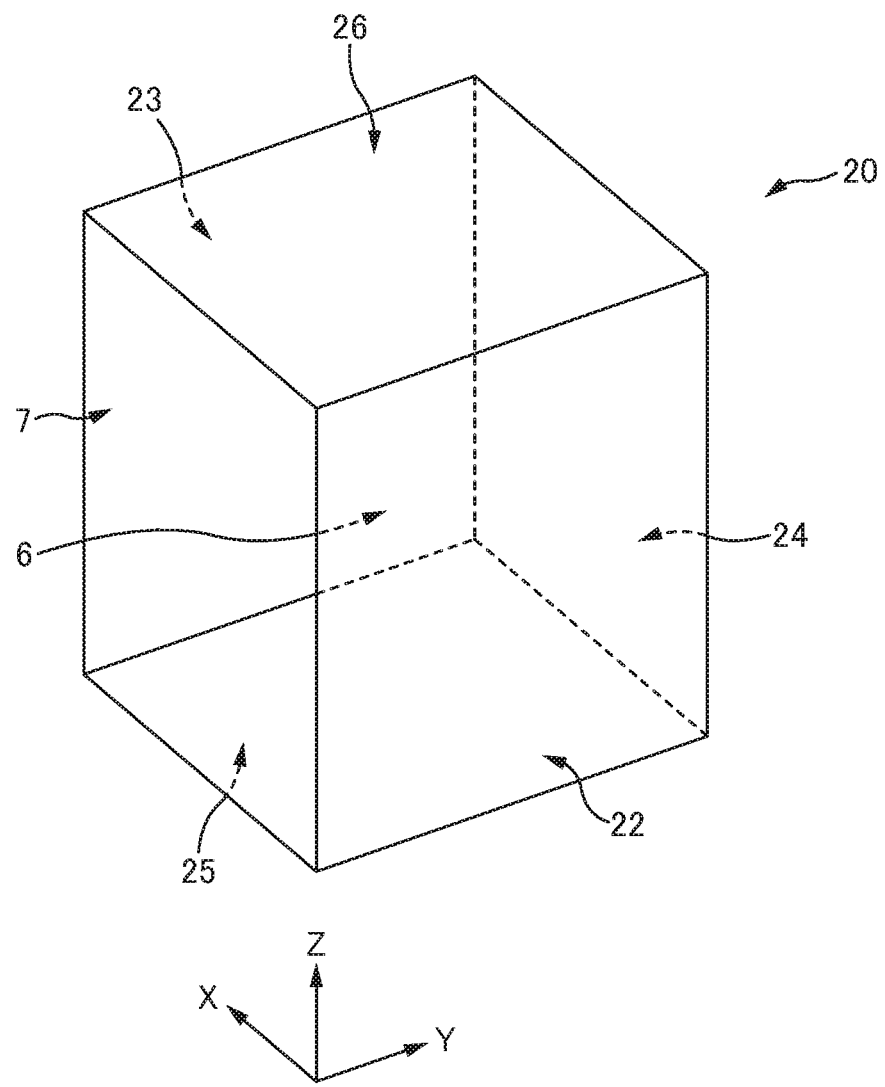
FIG. 4 is a diagram to explain an inner case of a culture apparatus according to an embodiment of the present disclosure.

FIGS. 1 and 2 are external perspective views illustrating the culture apparatus 1. FIG. 3 is a cross-sectional view illustrating the culture apparatus 1. FIG. 4 is a diagram to explain an inner case 20.

Note that, in an embodiment of the present disclosure, when facing an opening 7 of a heat-insulated case 2 in the culture apparatus 1, a width direction of the culture apparatus 1 is referred to as the X-axis direction, a depth direction of the culture apparatus 1 is referred to as the Y-axis direction, and a vertical direction thereof is referred to as the Z-axis direction. The opening 7 will be described later.

The culture apparatus 1 has a culture space 6 formed inside thereof, and includes a substantially box-shaped heat-insulated case (heat-insulated casing) 2 with the opening 7 in its front surface; and a heat-insulated door 3 which opens and closes freely the opening 7 of the heat-insulated case 2.

The heat-insulated case 2 includes a substantially box-shaped inner case 20 surrounding the culture space 6; and a substantially box-shaped outer case 10 surrounding the inner case 20.

The outer case 10 and the inner case 20 are substantially rectangular parallelepiped boxes. The inner case 20 is formed in a smaller size than that of the outer case 10 to be housed inside the outer case 10. An opening 7 leading to the culture space 6 is formed in the front surface of the outer case 10 and the inner case 20. The outer case 10 and the inner case 20 are made of metal such as stainless steel having resistance to hydrogen peroxide, ozone, ultraviolet ray as well as heat and bacteria.

A thermal insulating material 11 is disposed on an inner surface of the outer case 10, and an air layer (so-called air jacket) 12 is formed between the thermal insulating material 11 and an outer surface (rear surface) of the inner case 20.

One or more heaters 28 (one or more culture heaters 28A, one or more sterilization heaters 28B, which will be described later) to heat the culture space 6 are disposed on one or more outer surfaces (inner surfaces) of the inner case 20.

The inner case 20 includes a right side plate (right side surface) 22, a left side plate (left side surface) 23, a back plate (back surface) 24, a bottom plate (bottom surface) 25, and a top plate (top surface) 26. On each of the right side plate 22 and the left side plate 23, a plurality of the shelf rests 27 is formed by press working. One or more shelves 4 are to be placed on the shelf rests 27. The shelf rests 27 in pairs provided to the right side plate 22 and the left side plate 23 support the shelf 4 in a substantially horizontal manner.

Further, a humidification pan 5 in which water generated when the culture space 6 is humidified is stored is disposed in the culture space 6.

The heat-insulated door 3 includes an outer door 40 and an inner door 50.

The outer door 40 and the inner door 50 open and close the opening 7.

The outer door 40 is made of a metal material such as stainless steel, and is a substantially rectangular-shaped box having a form larger than that of the inner door 50. A thermal insulating material 11 and a heater 28 are provided across the air layer 12 inside the outer door 40. The heater 28 is provided on the rear side of an inner wall surface 43 of the outer door 40, the inner wall surface 43 facing the culture space when the door is closed.

An operation device 42 to operate the culture apparatus 1 is provided on an outer surface of the outer door 40. Further, a gasket 41 to ensure airtightness of the culture space 6 is provided on the inner side (on the side facing the opening 7) of the inner wall surface 43 of the outer door 40.

The inner door 50 has resistance to hydrogen peroxide, ozone, ultraviolet ray, etc., as well as heat and bacteria and is made of a material such as a transparent resin and glass. A gasket 13 is provided on the peripheral edge of the opening 7 of the front surface of the heat-insulated case 2 to ensure airtightness of the culture space 6 such that the gasket 13 faces the inner door 50 and attaches thereto when the door is closed.

The culture apparatus 1, for example, if it is a CO2 incubator, supplies CO2 gas into the culture space 6 to set/maintain CO2 at a predetermined concentration.

In the culture space 6, a duct 30, which is constituted by a back surface duct 30A and a bottom surface duct 30B, is disposed to have a space with the back plate 24 and the bottom plate 25 of the inner case 20, to form a gas passage K of air containing CO2, etc., along the back surface and the bottom surface of the culture space 6, respectively. In the culture apparatus 1, the air is forced to be circulated by drawing the gas containing CO2, etc., in the culture space 6 from an inlet 35 formed in an upper portion of the back surface duct 30A and blowing out the air into the culture space 6 through an outlet 36 provided in the front and side of the bottom surface duct 30B.

In the duct 30, a circulation blower 31 is disposed for the forced circulation of the gas containing CO2, etc. This circulation blower 31 includes a fan 31A, a motor 31B, and a shaft 31C. The motor 31B is disposed in a machine compartment 60 on the back of the heat-insulated case 2, which will be described later, and the shaft 31C extends from the motor 31B in this machine compartment 60 to the gas passage K of CO2, etc., through the back plate of the heat-insulated case 2 and is connected to the fan 31A.

Further, the humidification pan 5 with an opening on the top to store water for humidification (i.e., humidification water) 5A is disposed between the bottom surface duct 30B and the bottom plate 25 of the inner case 20. The humidification pan 5 is heated by the heater 28 disposed on the rear surface of the bottom plate 25 of the inner case 20 to evaporate water.

Note that the humidification pan 5 is disposed in the duct 30 on the bottom portion of the culture space 6; thereby, the humidified gas can be efficiently circulated into the gas passage K of CO2, etc., toward the culture space 6. The gas passage K is formed with the circulation blower 31 and the duct 30.

On the back of the outer case 10 of the heat-insulated case 2, the machine compartment 60 is formed with a back cover 14 covering the back of the outer case 10, and in the machine compartment 60, the motor 31B serving as a means to drive the circulation blower 31, a gas supply means 32 for supplying CO2 gas into the culture space 6, an internal temperature sensor 33 to measure temperature (internal temperature) of the culture space 6, and an electrical box 61 to accommodate electrical components such as a control device 62 are disposed.

The gas supply means 32 includes a gas supply pipe 32A, an on-off valve 32B, a filter 32C, and the like, and the tip of the gas supply pipe 32A faces the gas passage K.

In the culture apparatus 1, an ultraviolet lamp 34 is disposed in the gas passage K to sterilize the gas flowing through the culture space 6 and humidification water 5A in the humidification pan 5.

The culture apparatus 1 accepts instructions to start and stop the culture apparatus 1 and instruction inputs such as a target temperature (e.g., 37 degrees Celsius), a target humidity (e.g., 93% RH), and a target CO2 gas concentration (e.g., 5%) in the culture space 6 from the operation device 42 provided on the outer door 40. Then, the control device 62 controls the culture apparatus 1 so that temperature, humidity, CO2 concentration in the culture space 6 will reach the aforementioned target values.

Further, as illustrated in FIG. 3, the heaters 28 are connected to the control device (control unit) 62 in the machine compartment 60, via a heater through-hole 16 formed on the back of the outer case 10.

The heater through-hole 16 is covered with a heater cover 15 having heat-insulating properties which is provided in the machine compartment 60. The heater cover 15 is provided with a heater connector 29A. The heater connector 29A has one terminal connected to the heaters 28 and the other terminal connected to the control device 62 via a heater cable 29. Thus, the control device 62 and the heaters 28 are electrically connected.

The control device 62 controls electric supply of the heaters 28 such that temperature and/or humidity of the culture space 6 will be a target value, based on the internal temperature measured by the internal temperature sensor 33.

More specifically, the heaters 28 includes one or more culture heaters (first heater) 28A and one or more sterilization heaters (second heater) 28B.

The culture heater 28A is turned on when the culture apparatus 1 is operated in a "culture mode" and when it is operated in a "sterilization mode", which will be described later. Further, the sterilization heater 28B is turned on when the culture apparatus 1 is operated in the "sterilization mode", while the sterilization heater 28B is not turned on when the culture apparatus 1 is operated in the "culture mode".

In the culture mode, the temperature in the culture space 6 is controlled to be maintained at a temperature (the first temperature) suitable for performing culture in order to incubate a culture in the culture space 6. The first temperature is in a range from about a room temperature to about 50 degrees Celsius, and is, for example, 37 degrees Celsius.

The control device 62 turns on the culture heater 28A without turning on the sterilization heater 28B during the culture mode. When turning on the culture heater 28A, the control device 62 performs duty control of repeating an ON state (ON) and an OFF state (OFF) at a predetermined cycle.

Thus, the culture apparatus 1 can be controlled such that the temperature in the culture space 6 is maintained at the first temperature.

In the sterilization mode, the temperature in the culture space 6 is controlled to be maintained at a temperature (the second temperature higher than the first temperature) suitable for making the culture space 6 sterile in order to make the culture space 6 sterile. The second temperature is substantially equal to or higher than 100 degrees Celsius and is, for example, 180 degrees Celsius.

The control device 62 turns on the sterilization heater 28B and the culture heater 28A during the sterilization mode. When turning on the culture heater 28A, the control device 62 performs duty control of repeating an ON state (ON) and an OFF state (OFF) at a predetermined cycle. When turning on the sterilization heater 28B, the control device 62 controls the sterilization heater 28B such that the sterilization heater 28B is kept ON.

Thus, the culture apparatus 1 can be controlled such that the temperature in the culture space 6 is maintained at the second temperature that is higher than the first temperature.

Figure 5:
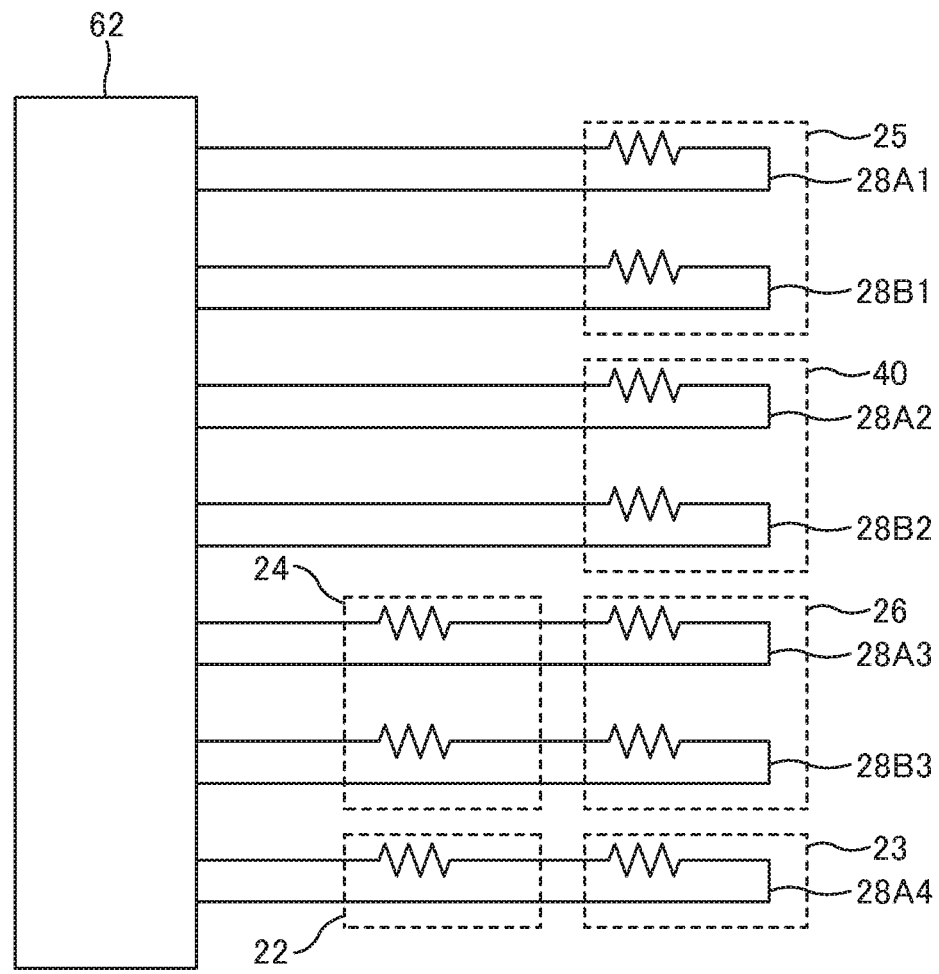
FIG. 5 is a diagram to explain a heater according to an embodiment of the present disclosure.
Figure 6:
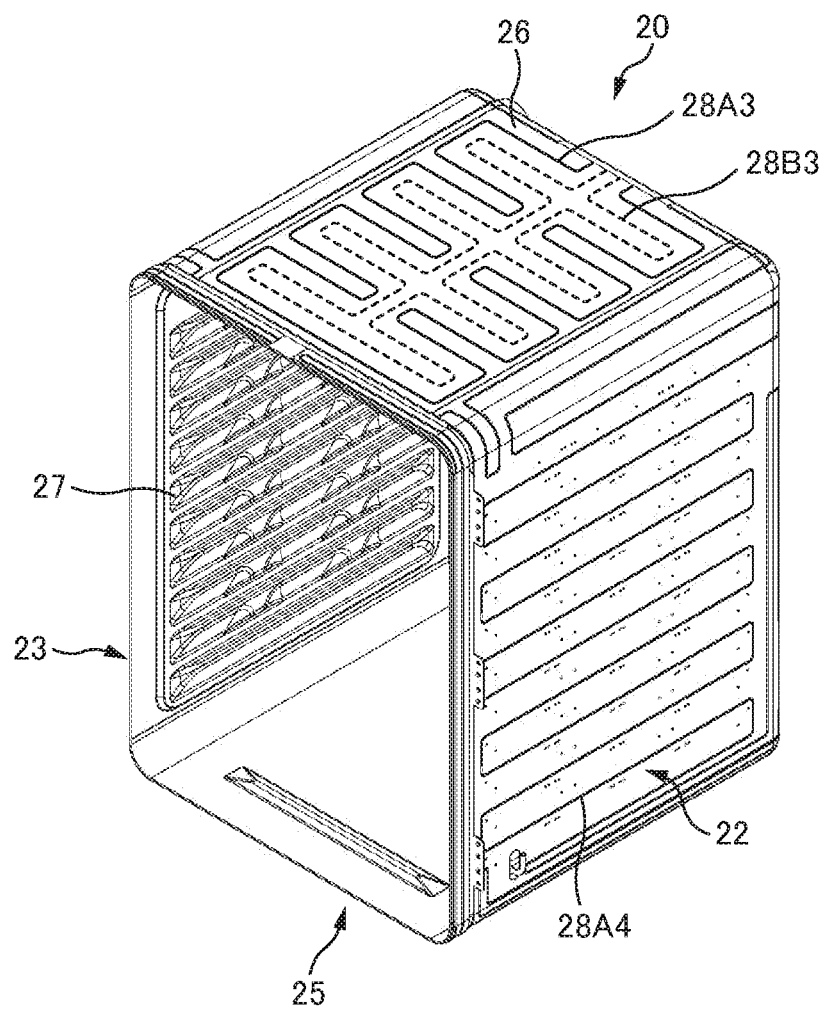
FIG. 6 is a diagram illustrating a state where a heater according to an embodiment of the present disclosure is disposed in an inner case.
Figure 7:
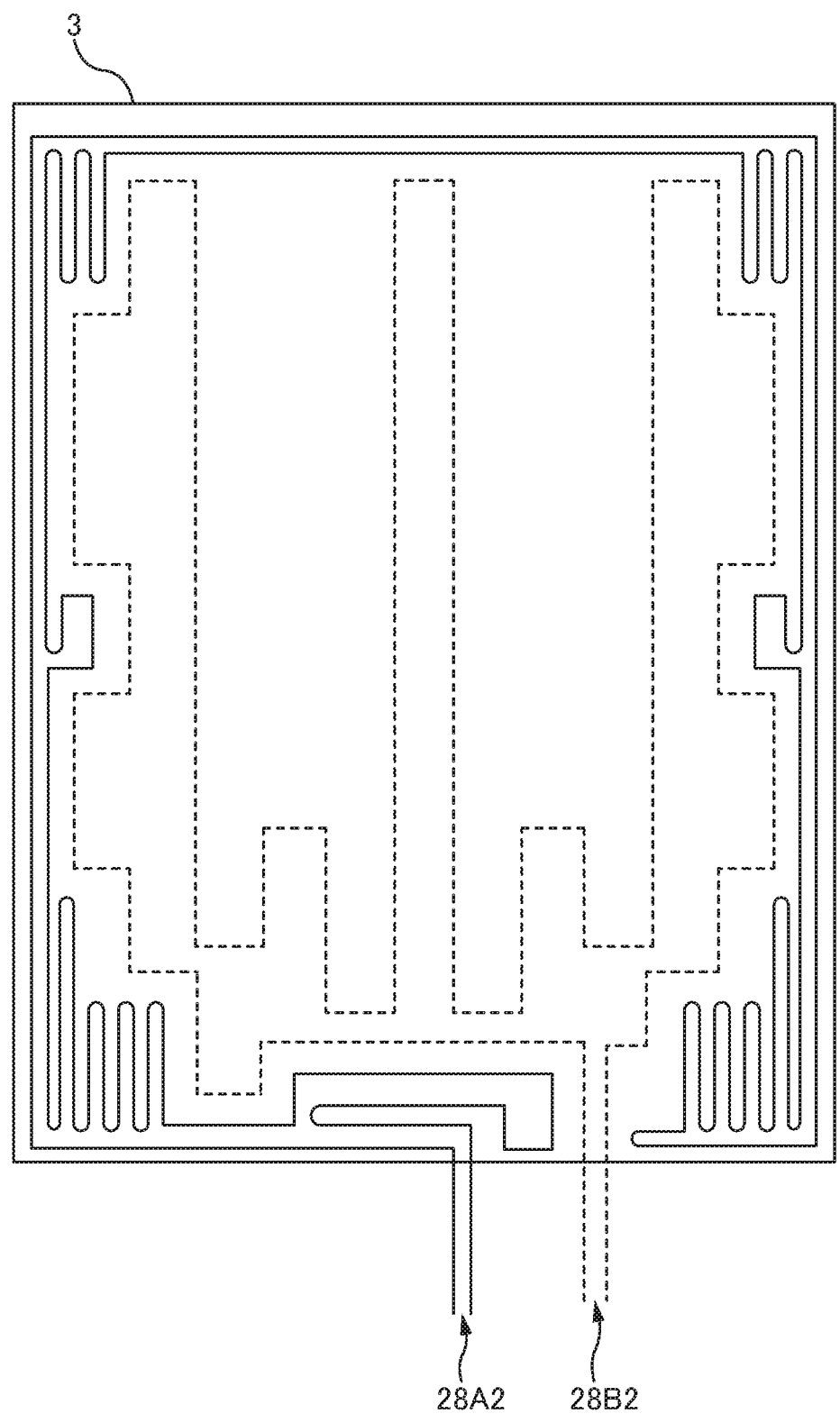
FIG. 7 is a diagram illustrating a state where a heater according to an embodiment of the present disclosure is disposed in a heat-insulated door.

Note that the culture heaters 28A and the sterilization heaters 28B are, as illustrated in FIGS. 5 to 7, connected to the control device 62 and are disposed to the surfaces of the inner case 20 and the outer door 40.

That is, first, as illustrated in FIG. 5, the culture heaters 28A includes: a bottom plate culture heater 28A1 disposed to the bottom plate 25 of the inner case 20, an outer door culture heater 28A2 disposed to the outer door 40, a top and back plate culture heater 28A3 disposed to the top plate 26 and the back plate 24 of the inner case 20, and a side plate culture heater 28A4 disposed to the right side plate 22 and the left side plate 23 of the inner case 20.

Further, the sterilization heaters 28B includes: a bottom plate sterilization heater 28B1 disposed to the bottom plate 25 of the inner case 20, an outer door sterilization heater 28B2 disposed to the outer door 40, a top and back plate sterilization heater 28B3 disposed to the top plate 26 and the back plate 24 of the inner case 20.

These culture heaters 28A and sterilization heaters 28B comprise a first system including the bottom plate culture heater 28A1 and the bottom plate sterilization heater 28B1; a second system including the outer door culture heater 28A2 and the outer door sterilization heater 28B2; a third system including the top and back plate culture heater 28A3 and the top and back plate sterilization heater 28B3; and a fourth system including the side plate culture heater 28A4. The control device 62 controls electric supply to the heaters 28 on an individual system basis, which will be described later.

Accordingly, by controlling the heaters 28 on an individual system basis, individual control of the heaters 28 corresponding to their installation locations and control of the temperature distribution in the culture space 6 at a high level become possible. For example, more uniform temperature distribution in the culture space 6 becomes possible.

In the culture apparatus 1 according to an embodiment of the present disclosure, the sterilization heater 28B is not provided to the right side plate 22 or the left side plate 23 of the inner case 20.

According to such an embodiment, as illustrated in FIG. 6, only the side plate culture heater 28A4 is provided to both side surfaces 22, 23 of the inner case 20. Thus, it is possible to ensure a space for press working to form the shelf rests 27 in both side surfaces 22, 23 of the inner case 20.

By forming the shelf rests 27 in both side surfaces 22, 23 of the inner case 20 by press working, the shelf rests 27 and the inner case 20 can be connected through an integral continuous surface without a boundary. This can facilitate prevention of adhesion and accumulation of bacteria, as well as removal thereof.

As described above, the side plate culture heater 28A4 provided to both side surfaces 22, 23 of the inner case 20 is controlled by the control device 62 as the fourth system independently of other systems. Thus, for example, a heater generating a larger amount of heat per unit time than the amount of heat generated by the culture heaters 28A of other systems can also be used as the side plate culture heater 28A4.

Thus, it becomes possible to prevent shortage of the amount of generated heat, which could be caused, for example, by no sterilization heater 28B provided to the side surfaces 22, 23 of the inner case 20 during the sterilization mode. On the other hand, during the culture mode, by controlling the duty cycle of the side plate culture heater 28A4 independently of the culture heaters 28A of other systems, the amount of generated heat is harmonized with the one by the culture heaters 28A of other systems and the temperature can be most suitably controlled in the culture space 6.

Further, as illustrated in FIG. 7, an outer door 3 is provided with the outer door culture heater 28A2 and the outer door sterilization heater 28B2 which belong to the second system. In an embodiment of the present disclosure, the outer door culture heater 28A2 is provided along the outer edges of the outer door 3, while the outer door sterilization heater 28B2 is provided closer to the center of the outer door 3.

According to such an embodiment, during the culture mode in which the temperature in the culture space 6 should be maintained at a predetermined degree suitable for incubating cultures, it becomes possible to effectively heat the vicinity of the outer edges of the outer door 3 where the temperature is likely to be relatively lowered. On the other hand, during the sterilization mode, it becomes possible to effectively raise the temperature in the culture space 6 up to the second temperature by heating the entire outer door 3 using both the outer door sterilization heater 28B2 and the outer door culture heater 28A2.

Next, control in each of the "culture mode" and the "sterilization mode" which are implemented by the culture apparatus 1 will be described with reference to FIGS. 8 to 10.

First, a structure of the control device 62 will be described with reference to FIG. 8. The control device 62 includes a mode determination unit 62A and a heater control unit 62B.

When the culture apparatus 1 is started, the mode determination unit 62A receives an operation input from the operation device 42 and determines whether an operator of the culture apparatus 1 has selected the "sterilization mode". In an embodiment of the present disclosure, the mode determination unit 62A, after the culture apparatus 1 is started, determines that the "culture mode" has been selected as long as the "sterilization mode" is not selected. That is, the mode determination unit 62 determines that the "sterilization mode" has been selected only when receiving, from the operation device 42, an operation input indicative that the "sterilization mode" has been selected. Then, the determination made by the mode determination unit 62A is transmitted to the heater control unit 62B.

The heater control unit 62B controls the culture heater 28A and the sterilization heater 28B in accordance with the determination of the control mode transmitted from the mode determination unit 62A.

Such control of the culture heater 28A and the sterilization heater 28B performed by the heater control unit 62B in accordance with the control mode will be described in detail with reference to FIG. 9.

Figures 8, 9:
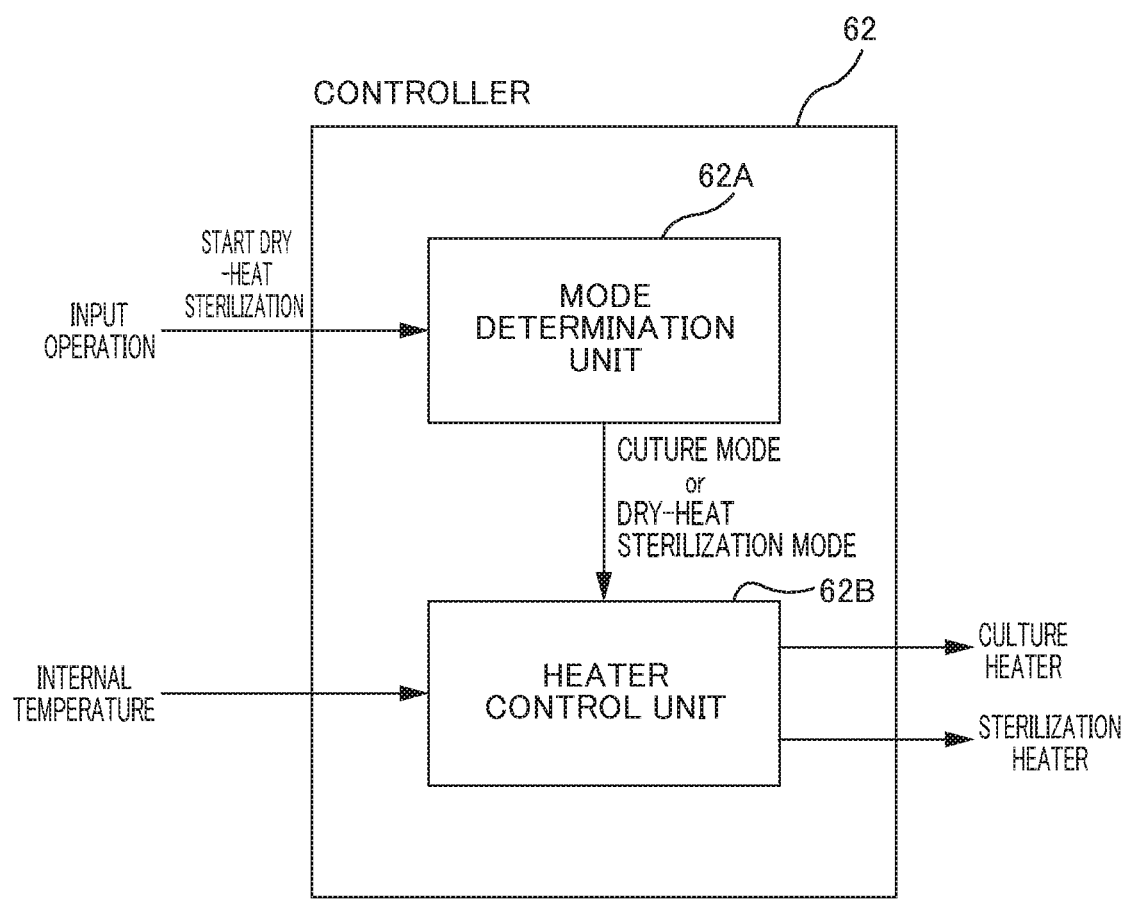
FIG. 8 is a diagram to explain a control device according to an embodiment of the present disclosure.
FIG. 9 is a diagram to explain a control mode of a heater according to an embodiment of the present disclosure.

FIG. 9 illustrates the details of control of the culture heater 28A and the sterilization heater 28B for both the case that the "culture mode" is selected and the case that the "sterilization mode" is selected.

First, the case of the "culture mode" will be described. In this case, the heater control unit 62B turns on the culture heaters 28A under duty control, and does not turn on (OFF) the sterilization heater 28B. That is, the heater control unit 62B performs control to make the temperature in the culture space 6 the first temperature only using the culture heater 28A. The heater control unit 62B controls to make the internal temperature the first temperature, by controlling the duty cycle of the culture heater 28A, for example, under PID control, in accordance with the difference between the temperature measured by the internal temperature sensor 33 and the target temperature.

Figure 10:
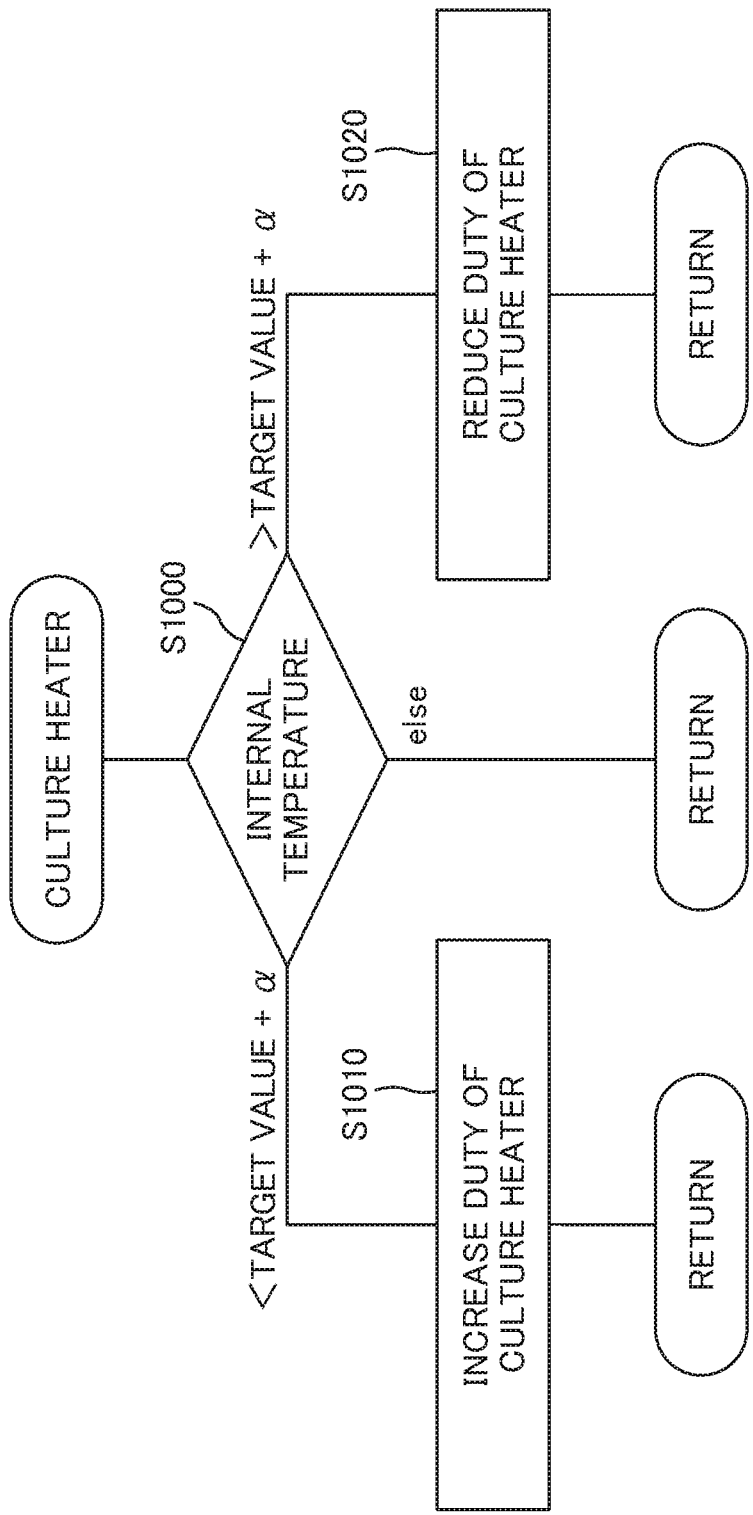
FIG. 10 is a flow chart to explain a flow of control of a heater according to an embodiment of the present disclosure.

FIG. 10 illustrates a process when the heater control unit 62B performs duty control over the culture heater 28A.

When the internal temperature is lower than a target value−α (α is a predetermined temperature, for example, 0.1 degree Celsius) (S1000), the heater control unit 62B increases the duty cycle of the culture heater 28A (S1010). Whereas, when the internal temperature is higher than the target value+α, the heater control unit 62B reduces the duty cycle of the culture heater 28A (S1020). Under such control, the heater control unit 62B can maintain the internal temperature in a range of the target value±α.

Returning to FIG. 9, the case where the "sterilization mode" has been selected will be described. In this case, the heater control unit 62B turns on the culture heater 28A under duty control, and keeps the sterilization heater 28B ON. That is, using both the culture heater 28A and the sterilization heater 28B, the heater control unit 62B controls the temperature in the culture space 6 to make it the second temperature. The heater control unit 62B drives the sterilization heater 28B to promote increase in the internal temperature, while it controls the internal temperature to make it the second temperature by controlling the duty cycle of the culture heater 28A, for example, under PID control in accordance with a difference between the temperature measured by the internal temperature sensor 33 and the target temperature. The details of the duty control of the culture heater 28A performed by the heater control unit 62B during the "sterilization mode" is similar to the control during the "culture mode" described in FIG. 10, except that the target temperatures are different.

As has been described above, according to the culture apparatus 1 of an embodiment of the present disclosure, the heaters 28 to heat the culture space 6 includes the culture heater 28A and the sterilization heater 28B, which makes it possible to perform efficient control with their streamlined combinations in accordance with the target temperature of the culture space 6. For example, in the culture mode, the culture heater 28A is turned on without turning on the sterilization heater 28B, while in the sterilization mode, both the sterilization heater 28B and the culture heater 28A are turned on; thereby, the culture apparatus 1 can be efficiently controlled.

Further, as shown in the culture apparatus 1 according to an embodiment of the present disclosure, the sterilization heater 28B is not provided to the right side plate 22 and the left side plate 23 of the inner case 20; thereby, it becomes possible to ensure a space for press working to form the shelf rests 27 in both side surfaces 22, 23 of the inner case 20. Then, the shelf rests 27 in both side surfaces 22, 23 of the inner case 20 are formed by press working; thereby, the shelf rests 27 and the inner case 20 can be seamlessly connected as an integral continuous surface. This can facilitate prevention of adhesion and accumulation of bacteria as well as removal thereof.

Further, as in the culture apparatus 1 according to an embodiment of the present disclosure, the culture heater 28A and the sterilization heater 28B are divided into a plurality of systems according to their installation locations, and the control device 62 controls ON/OFF to the heaters 28 on an individual system basis. This makes it possible to individually control the heaters 28 according to their installation locations, thereby being able to control temperature distribution in the culture space 6 more highly, for example, in more uniform manner.

Further, as shown in the culture apparatus 1 according to an embodiment of the present disclosure, a heater generating a larger amount of heat per unit time than those generated by the culture heaters 28A of other systems can also be used as the side plate culture heater 28A4.

Thus, it becomes possible to prevent shortage of generated heat, which could be caused by no sterilization heater 28B provided to the side surfaces of the inner case 20, for example, during the sterilization mode. On the other hand, during the culture mode, by controlling the duty cycle of the side plate culture heater 28A4 independently of the culture heaters 28A of other systems, the generated heat is harmonized with the one of the culture heaters 28A of other systems and the temperature is most suitably controlled in the culture space 6.

Second Embodiment

Next, a second embodiment will be described. Note that, in the second embodiment, regarding the drawings common to those in the first embodiment, those in the first embodiment will be suitably referred in describing the second embodiment.

FIGS. 1 and 2 are external perspective views of the culture apparatus 1. FIG. 3 is a cross-sectional view illustrating the culture apparatus 1. FIG. 4 is a diagram to explain the inner case 20.

Note that, in an embodiment of the present disclosure, when facing an opening 7 of a heat-insulated case 2 in the culture apparatus 1, a width direction of the culture apparatus 1 is referred to as the X-axis direction, a depth direction of the culture apparatus 1 is referred to as the Y-axis direction, and a vertical direction thereof is referred to as the Z-axis direction. The opening 7 will be described later.

The culture apparatus 1 has a culture space 6 formed inside thereof, and includes a substantially box-shaped heat-insulated case 2 with the opening 7 in its front surface; and a heat-insulated door 3 which opens and closes freely the opening 7 of the heat-insulated case 2.

The heat-insulated case 2 includes a substantially box-shaped inner case 20 having the culture space 6 formed inside thereof; and a substantially box-shaped outer case 10 formed to cover the inner case 20.

The outer case 10 and the inner case 20 are substantially rectangular parallelepiped boxes. The inner case 20 is formed in a smaller size than that of the outer case 10 to be housed inside the outer case 10. An opening 7 leading to the culture space 6 is formed in the front surfaces of the outer case 10 and the inner case 20. The outer case 10 and the inner case 20 are made of metal such as stainless steel having resistance to hydrogen peroxide, ozone, ultraviolet ray as well as heat and bacteria.

A thermal insulating material 11 is disposed on the inner surface of the outer case 10, and an air layer (so-called air jacket) 12 is formed between the thermal insulating material 11 and the outer surface of the inner case 20.

The heaters 28 (the culture heaters 28A, the sterilization heaters 28B, which will be described later) to heat the culture space 6 is disposed on the outer surfaces of the inner case 20.

The inner case 20 includes a right side plate 22, a left side plate 23, a back plate 24, a bottom plate 25, and a top plate 26. On each of the right side plate 22 and the left side plate 23, a plurality of the shelf rests 27 is formed by press working. One or more shelves 4 are placed on the shelf rests 27. The shelf rests 27 in pairs provided to the right side plate 22 and the left side plate 23 support the shelf 4 in a substantially horizontal manner.

Further, a humidification pan 5 in which water generated when the culture space 6 is humidified is stored is disposed in the culture space 6.

The heat-insulated door 3 includes an outer door 40 and an inner door 50.

The outer door 40 and the inner door 50 open/close the opening 7.

The outer door 40 is made of a metal material such as stainless steel, and is a substantially rectangular-shaped box having a form larger than that of the inner door 50. A thermal insulating material 11 and a heater 28 are provided inside the outer door 40.

An operation device 42 to operate the culture apparatus 1 is provided on the outer surface of the outer door 40. Further, a gasket 41 to ensure airtightness of the culture space 6 is provided on a surface facing the opening 7 of the outer door 40.

The inner door 50 has resistance to hydrogen peroxide, ozone, ultraviolet ray, etc., as well as heat and bacteria and is made of a material such as a transparent resin and glass. A gasket 13 is provided on the peripheral edge of the opening 7 of the front surface of the heat-insulated case 2 to ensure airtightness of the culture space 6 such that the gasket 13 faces the inner door 50 and attaches thereto when the door is closed.

The culture apparatus 1, for example, if it is a CO2 incubator, supplies CO2 gas into the culture space 6 to set/maintain CO2 at a predetermined concentration.

In the culture space 6, a duct 30, which is constituted by a back surface duct 30A and a bottom surface duct 30B, is disposed to have a space with the back plate 24 and the bottom plate 25 of the inner case 20, to form a gas passage K of air containing CO2, etc., along the back surface and the bottom surface of the culture space 6, respectively. In the culture apparatus 1, the air is forced to be circulated by drawing the gas containing CO2, etc., in the culture space 6 from an inlet 35 formed in an upper portion of the back surface duct 30A and blowing out the air into the culture space 6 through an outlet 36 provided in the front and side of the bottom surface duct 30B.

In the duct 30, a circulation blower 31 is disposed for the forced circulation of the gas containing CO2, etc. This circulation blower 31 includes a fan 31A, a motor 31B, and a shaft 31C. The motor 31B is disposed in a machine compartment 60 on the back of the heat-insulated case 2, which will be described later, and the shaft 31C extends from the motor 31B in this machine compartment 60 to the gas passage K of CO2, etc., through the back plate of the heat-insulated case 2 and is connected to the fan 31A.

Further, the humidification pan 5 with an opening on the top to store water for humidification (i.e., humidification water) 5A is disposed between the bottom surface duct 30B and the bottom plate 25 of the inner case 20. The humidification pan 5 is heated by the heater 28 disposed on the inner surface of the bottom plate 25 of the inner case 20 to evaporate water.

Note that the humidification pan 5 is disposed in the duct 30 on the bottom portion of the culture space 6; thereby, the humidified gas can be efficiently circulated into the gas passage K of CO2, etc., toward the culture space 6. The gas passage K is formed with the circulation blower 31 and the duct 30.

On the back of the outer case 10 of the heat-insulated case 2, the machine compartment 60 is formed with a back cover 14 covering the back of the outer case 10, and in the machine compartment 60, the motor 31B serving as a means to drive the circulation blower 31, a gas supply means 32 for supplying CO2 gas into the culture space 6, an internal temperature sensor 33 to measure temperature (internal temperature) of the culture space 6, and an electrical box 61 to accommodate electrical components such as a control device 62 are disposed.

The gas supply means 32 includes a gas supply pipe 32A, an on-off valve 32B, a filter 32C, and the like, and the tip of the gas supply pipe 32A faces the gas passage K.

In the culture apparatus 1, an ultraviolet lamp 34 is disposed in the gas passage K to sterilize the gas flowing through the culture space 6 and humidification water 5A in the humidification pan 5.

The culture apparatus 1 accepts instructions to start and stop the culture apparatus 1 and instruction inputs such as a target temperature (e.g., 37 degrees Celsius), a target humidity (e.g., 93% RH), and a target CO2 gas concentration (e.g., 5%) in the culture space 6 from the operation device 42 provided on the outer door 40. Then, the control device 62 controls the culture apparatus 1 so that temperature, humidity, CO2 concentration in the culture space 6 will reach the aforementioned target values.

Further, as illustrated in FIG. 3, the heaters 28 are connected to the control device 62 in the machine compartment 60, via a heater through-hole 16 formed on the back of the outer case 10.

The heater through-hole 16 is covered with a heater cover 15 having heat-insulating properties that is provided in the machine compartment 60. The heater cover 15 is provided with a heater connector 29A. The heater connector 29A has one terminal connected to the heaters 28 and the other terminal connected to the control device 62 via a heater cable 29. Thus, the control device 62 and the heaters 28 are electrically connected.

The control device 62 controls ON/OFF of the heaters 28 such that temperature and/or humidity of the culture space 6 will be a target value, based on the internal temperature measured by the internal temperature sensor 33.

More specifically, the heaters 28 includes the culture heaters (first heater) 28A and the sterilization heaters (second heater) 28B.

The culture heater 28A is driven when the culture apparatus 1 is operated in a "culture mode (first mode)" and when operated in a "sterilization mode (second mode)", which will be described later. Further, the sterilization heater 28B is driven when the culture apparatus 1 is operated in the "sterilization mode", while the sterilization heater 28B is not driven when the culture apparatus 1 is operated in the "culture mode".

Note that, in an embodiment of the present disclosure, it is assumed that the overall power consumption of the culture heater 28A is 360 W, while the overall power consumption of the sterilization heater 28B is also 360 W.

In the culture mode the temperature in the culture space 6 is controlled to be maintained at a temperature (the first temperature) suitable for performing culture in order to incubate a culture in the culture space 6. The first temperature is in a range from about a room temperature to about 50 degrees Celsius and is, for example, 37 degrees Celsius.

The control device 62 drives the culture heater 28A without driving the sterilization heater 28B during the culture mode. For the culture heater 28A, the control device 62 performs duty control of repeating an ON state (ON) and an OFF state (OFF) at a predetermined cycle.

Thus, the culture apparatus 1 can be controlled such that the temperature in the culture space 6 is maintained at the first temperature.

In the sterilization mode, the temperature in the culture space 6 is controlled to be maintained at a temperature (the second temperature) suitable for making the culture space 6 sterile in order to make the culture space 6 sterile. The second temperature is substantially equal to or higher than 100 degrees Celsius and is, for example, 180 degrees Celsius.

The control device 62 drives the sterilization heater 28B and the culture heater 28A during the sterilization mode. For the culture heater 28A, the control device 62 performs duty control of repeating an ON state (ON) and an OFF state (OFF) at a predetermined cycle. For the sterilization heater 28B, the control device 62 controls the sterilization heater 28B such that the sterilization heater 28B is kept ON.

Thus, the culture apparatus 1 can be controlled such that the temperature in the culture space 6 is maintained at the second temperature that is higher than the first temperature.

Note that the culture heaters 28A and the sterilization heaters 28B are, as illustrated in FIGS. 5 and 6, connected to the control device 62 and are disposed to the surfaces of the inner case 20 and the outer door 40.

That is, as illustrated in FIG. 5, the culture heaters 28A includes: a bottom plate culture heater 28A1 disposed to the bottom plate 25 of the inner case 20, an outer door culture heater 28A2 disposed to the outer door 40, a top and back plate culture heater 28A3 disposed to the top plate 26 and the back plate 24 of the inner case 20, and a side plate culture heater 28A4 disposed to the right side plate 22 and the left side plate 23 of the inner case 20.

Further, the sterilization heater 28B includes: a bottom plate sterilization heater 28B1 disposed to the bottom plate 25 of the inner case 20, an outer door sterilization heater 28B2 disposed to the outer door 40, a top and back plate sterilization heater 28B3 disposed to the top plate 26 and the back plate 24 of the inner case 20. No sterilization heater 28B is disposed on the right side plate 22 or the left side plate 23 of the inner case 20.

Next, control in each of the "culture mode" and the "sterilization mode" which are implemented by the culture apparatus 1 will be described with reference to FIG. 8 and FIGS. 10 to 12.

First, a structure of the control device 62 will be described with reference to FIG. 8. The control device 62 includes a mode determination unit 62A and a heater control unit 62B.

When the culture apparatus 1 is started, the mode determination unit 62A receives an operation input from the operation device 42 and determines whether an operator of the culture apparatus 1 has selected the "sterilization mode". In an embodiment of the present disclosure, the mode determination unit 62A, after the culture apparatus 1 is started, determines that the "culture mode" has been selected as long as the "sterilization mode" is not selected. That is, the mode determination unit 62 determines that the "sterilization mode" has been selected only when receiving, from the operation device 42, an operation input indicative that the "sterilization mode" has been selected. Then, the determination made by the mode determination unit 62A is transmitted to the heater control unit 62B.

The heater control unit 62B controls the culture heater 28A and the sterilization heater 28B in accordance with the determination of the control mode transmitted from the mode determination unit 62A.

Such control of the culture heater 28A and the sterilization heater 28B performed by the heater control unit 62B in accordance with the control mode will be described in detail with reference to FIG. 11.

FIG. 11 illustrates the details of control of the culture heater 28A and the sterilization heater 28B for the case that the culture apparatus is "OFF", the case that the "culture mode" is selected, and the case that the "sterilization mode" is selected.

First, the case that the culture apparatus 1 is "OFF" will be described. In this case, since the culture apparatus 1 is not functioning, neither the culture heater 28A nor the sterilization heater 28B is turned on (OFF). Since both the culture heater 28A and the sterilization heater 28B are OFF, the power consumption is 0 W.

Next, the case of the "culture mode" will be described. In this case, the heater control unit 62B drives the culture heater 28A under duty control, and does not turn on (OFF) the sterilization heater 28B. That is, the heater control unit 62B performs control to make the temperature in the culture space 6 will be the first temperature only using the culture heater 28A. The heater control unit 62B controls to make the internal temperature the first temperature, by controlling the duty cycle of the culture heater 28A, for example, under PID control, in accordance with the difference between the temperature measured by the internal temperature sensor 33 and the target temperature.

FIG. 10 illustrates a process when the heater control unit 62B performs duty control over the culture heater 28A.

When the internal temperature is lower than a target value−α (α is a predetermined temperature, for example, 0.1 degree Celsius) (S1000), the heater control unit 62B increases the duty cycle of the culture heater 28A (S1010). Whereas, when the internal temperature is higher than the target value+α, the heater control unit 62B reduces the duty cycle of the culture heater 28A (S1020). Under such control, the heater control unit 62B can maintain the internal temperature in a range of the target value±α.

Returning to FIG. 11, the power consumption during this "culture mode", i.e., the power consumption of the culture heater 28A, is 360 W.

Specifically, the culture heater 28A is duty-controlled, and thus the culture heater 28A repeats an ON state (ON) and an OFF state (OFF) at a predetermined cycle. When the culture heater 28A is OFF, the power consumption of the culture heater 28A is 0 W; however, when the culture heater 28A is ON, the power consumption of the culture heater 28A is 360 W.

Next, the case where the "sterilization mode" is selected will be described. In this case, the heater control unit 62B drives the culture heater 28A under duty control, keeps driving the sterilization heater 28B ON. That is, using both the culture heater 28A and the sterilization heater 28B, the heater control unit 62B controls the temperature in the culture space 6 to make it the second temperature. The heater control unit 62B drives the sterilization heater 28B to promote increase in the internal temperature, while it controls the internal temperature to make it the second temperature by controlling the duty cycle of the culture heater 28A, for example, under PID control in accordance with a difference between the temperature measured by the internal temperature sensor 33 and the target temperature. The details of the duty control of the culture heater 28A performed by the heater control unit 62B during the "sterilization mode" is similar to the control during the "culture mode" described in FIG. 10, except for the target temperature being different.

Then, at this time, the power consumption during the "sterilization mode", i.e., the power consumption of the culture heater 28A and the sterilization heater 28B, is 720 W.

Specifically, since the sterilization heater 28B is kept in the ON state (ON), the power consumption of the sterilization heater 28B is continually 360 W. However, since the culture heater 28A is duty-controlled, the culture heater 28A repeats an ON state (ON) and an OFF state (OFF) at a predetermined cycle. When the culture heater 28A is in the OFF state, the total power consumption of the culture heater 28A and the sterilization heater 28B is 360 W, and when the culture heater 28A is in the ON state, the total power consumption is 720 W (360 W+360 W).

Figure 12:
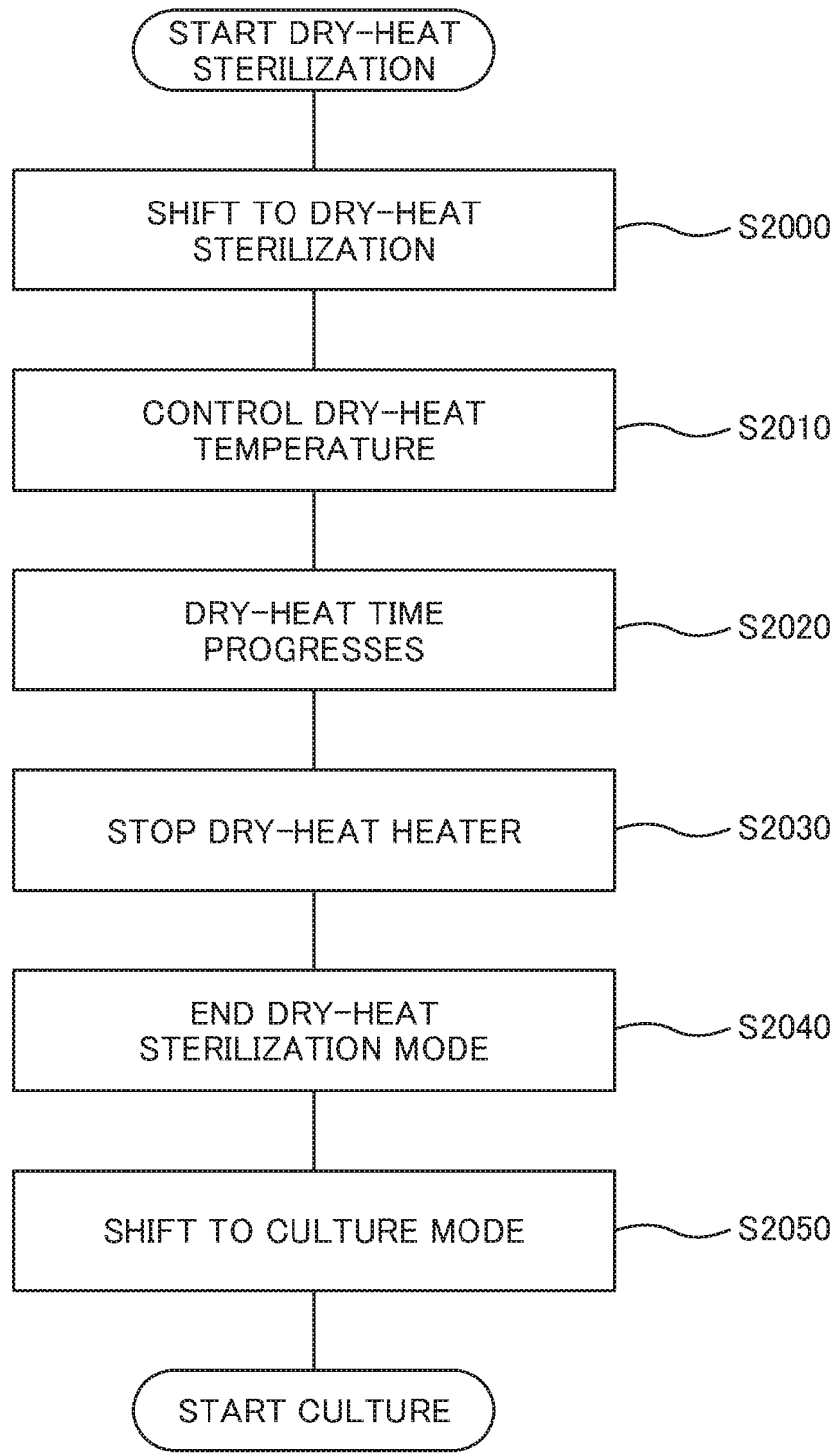
FIG. 12 is a flow chart to explain a flow of control of an embodiment of the present disclosure.

Further, FIG. 12 illustrates a flow of a process in the "sterilization mode" according to an embodiment of the present disclosure.

First, when the culture apparatus 1 receives an operation input from the operation device 42 and determines that an operator of the culture apparatus 1 has selected "the sterilization mode", the mode is shifted to the "sterilization mode" (S2000).

Then, the culture apparatus 1 starts performing dry-heat temperature control (S2010). The dry-heat temperature control means, as described above, performing control so that the heater control unit 62B drives the culture heater 28A under duty control and drives the sterilization heater 28B in the ON state (ON).

Then, the culture apparatus 1 maintains the internal temperature at the second temperature (for example, 180 degrees Celsius) during a predetermined period of time (dry-heat time) (S2020). The dry-heat time is, for example, one hour.

When the dry-heat time has been elapsed, the driving of the culture heater 28A and the sterilization heater 28B (S2030) is stopped in the culture apparatus 1.

According to such an embodiment, since the internal temperature is maintained at the second temperature during the dry-heat time, it becomes possible to reliably kill bacteria and microorganisms having entered the apparatus.

Then, when the internal temperature drops to a third temperature (for example, 40 degrees Celsius) that is lower than the second temperature, the culture apparatus 1 ends the sterilization mode (S2040), and starts the culture mode (S2050).

According to such an embodiment, the apparatus is maintained in a high temperature state also during a time period in which the internal temperature drops from the second temperature to the third temperature. Thus, sterilization in the apparatus is performed more reliably.

Further, when the internal temperature has reached the third temperature, the mode is automatically shifted to the culture mode. Accordingly, after the sterilization process is completed, the internal temperature is automatically shifted to the first temperature that is suitable for performing culture. Thus, for example, if the sterilization process in the culture space 6 is performed at night or on holidays when workers are absent, the temperature in the culture space 6 will be the first temperature that is suitable for performing culture, on the following day or after holidays, so that a worker can immediately start performing a cell culture.

As has been described above, according to the culture apparatus 1 of an embodiment of the present disclosure, the heaters 28 for heating the culture space 6 includes the culture heater 28A and the sterilization heater 28B, and the culture heater 28A is driven without driving the sterilization heater 28B in the culture mode, while both the sterilization heater 28B and the culture heater 28A are driven in the sterilization mode, so that the power consumption in the culture apparatus 1 can be reduced.

Next, another culture apparatus 1000 will be described to be compared with the culture apparatus 1 according to an embodiment of the present disclosure.

In such culture apparatuses 1000, a heater 1028 common to both the "culture mode" and the "sterilization mode" is used to heat its culture space.

This common heater 1028 has to be able to heat the culture spaces of the culture apparatuses 1 to the second temperature in the "sterilization mode". Thus, this heater 1028 is a heater corresponding to 720 W which is obtained by combining 360 W of the culture heater 28A and 360 W of the sterilization heater 28B which are used for the culture apparatus 1 to heat the culture space 6 to the second temperature.

The power consumption of the culture apparatus 1000 will be described with reference to FIGS. 13, 14.

Figure 13:
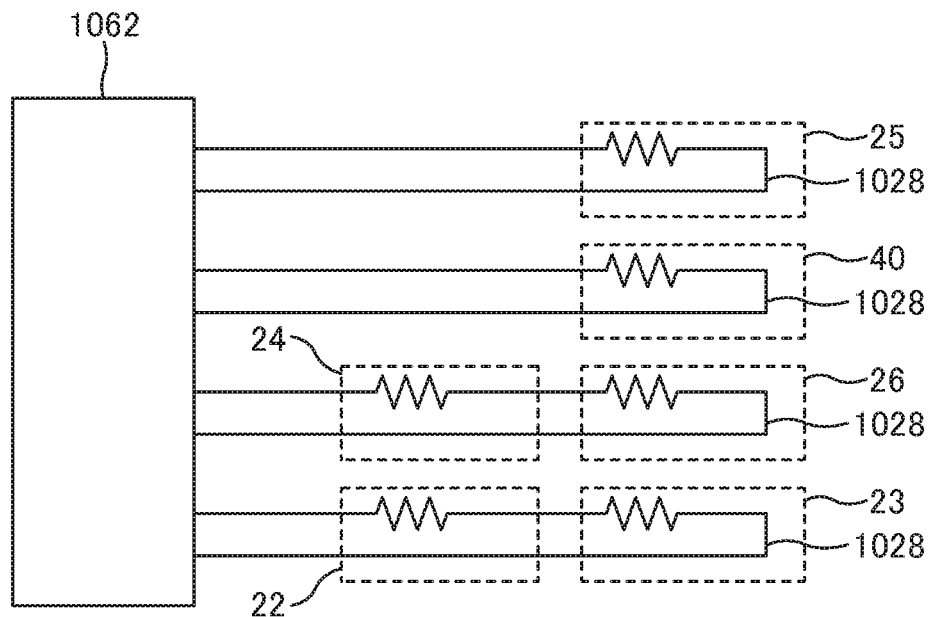
FIG. 13 is a diagram to explain a heater according to another embodiment.

First, as illustrated in FIG. 13, in the other culture apparatus 1000, such common heaters 1028 are disposed on the surfaces of the inner case 20 and the outer door 40.

Specifically, the culture apparatus 1000 includes: the heater 1028 disposed to the bottom plate 25 of the inner case 20; the heater 1028 disposed to the outer door 40; the heater 1028 disposed to the top plate 26 and the back plate 24 of the inner case 20; and the heater 1028 disposed to the right side plate 22 and the left side plate 23 of the inner case 20.

Next, FIG. 14 illustrates the details of control performed over the heater 1028 by a control device 1062 of the culture apparatus 1000.

FIG. 14 illustrates the power consumption and the details of control over the heater 1028 in each of the case where the culture apparatus 1000 is "OFF", the case where the "culture mode" is selected, and the case where the "sterilization mode" is selected.

First, the case where the culture apparatus 1000 is "OFF" will be described. In this case, the control device 1062 does not drive any of the heaters 1028 (OFF). Then, at this time, since all of the heaters 1028 are OFF, the power consumption is 0 W.

Next, the case where the "culture mode" has been selected will be described. In this case, the control device 1062 drives the heaters 1028 under duty control. The control device 1062 controls the duty cycle of the heater 1028, for example, under PID control, according to the difference between the temperature measured by the internal temperature sensor 33 and the target temperature, so that the internal temperature will be controlled at the first temperature The power consumption during this "culture mode", i.e., the power consumption of the heater 1028, is 720 W.

That is, the heater 1028 is duty-controlled, and thus the heater 1028 repeats an ON state (ON) and an OFF state (OFF) at predetermined cycles. When the heater 1028 is in the OFF state, the power consumption of the heater 1028 is 0 W, however, when the heater 1028 is in the ON state, the power consumption of the heater 1028 is 720 W.

Next, the case where the "sterilization mode" has been selected will be described. In this case as well, the control device 1062 drives the heater 1028 under duty control. The control device 1062 controls the duty cycle of the heaters 1028, for example, under PID control, according to a difference between the temperature measured by the internal temperature sensor 33 and the target temperature, so that the internal temperature will be controlled at the second temperature.

Thus, the power consumption during the "sterilization mode", i.e., the power consumption of the heater 1028, is 720 W.

As such, in the culture apparatus 1000, the power consumption of the heater is 720 W in both the "culture mode" and "the sterilization mode".

Accordingly, in the culture apparatus 1000, even if control is performed to shorten the time period of the ON state of the heater 1028, in order to reduce the calorific value of the large capacity heater 1028 in the "culture mode", a current having a predetermined size flows in the heater 1028 while the heater 1028 is in an ON state, which increases the power consumption of the culture apparatus 1000.

Thus, when introducing the culture apparatus 1000 of such a type that the culture space 6 is made sterile with a large capacity heater 1028, it may be necessary to reinforce an electric power system of a building.

Furthermore, since it is impossible to incubate a culture using the culture apparatus 1000 during the sterilization of the culture space 6, it may also be necessary to introduce a plurality of culture apparatuses 1000 in order to continually incubate a culture, which may require further reinforcement of the electric power system.

Figure 15A:
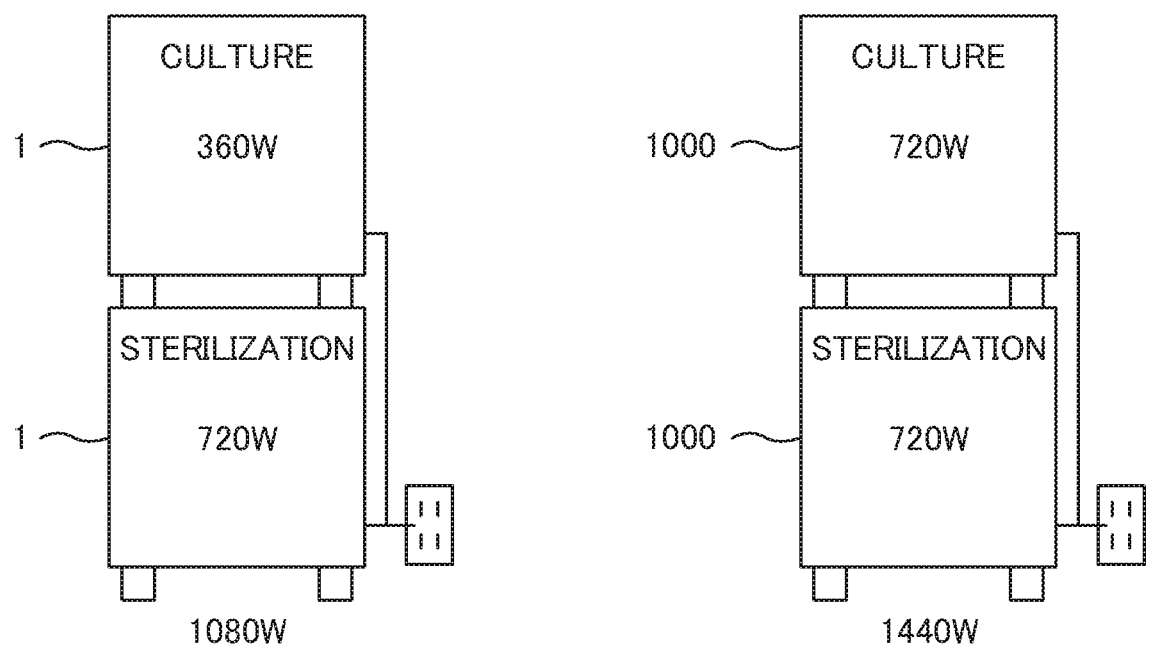
FIG. 15A is a diagram to explain power consumption of a culture apparatus.
Figure 15B:
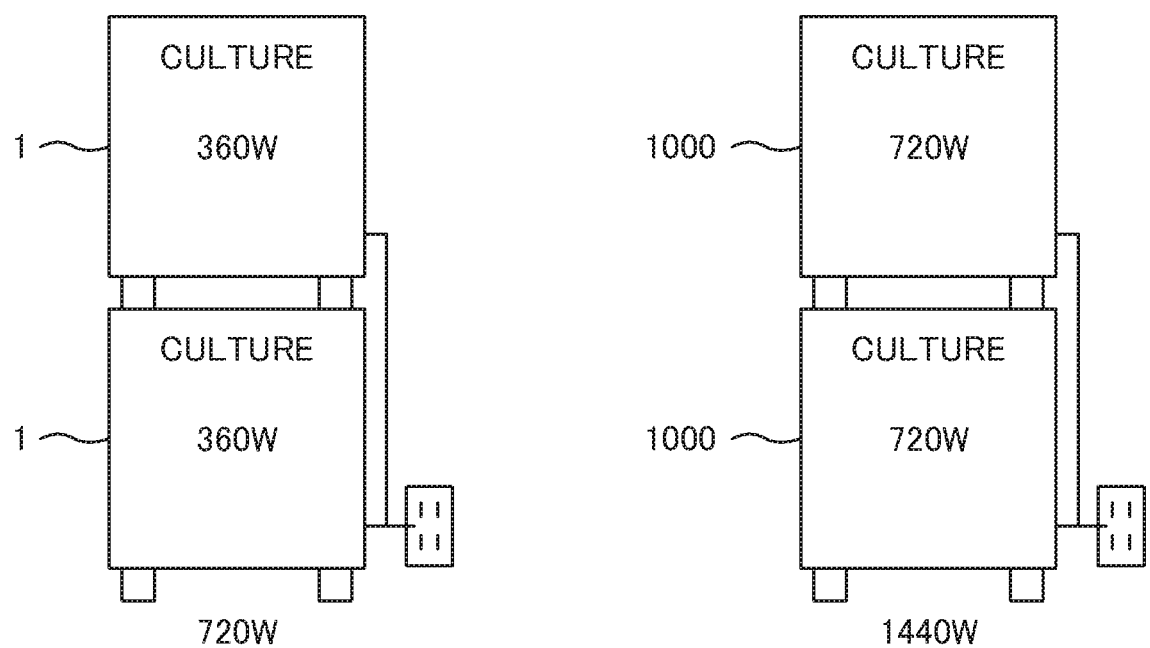
FIG. 15B is a diagram to explain power consumption of a culture apparatus.

Next, in FIGS. 15A and 15B, illustrated are comparison results of the power consumptions between the cases where two culture apparatuses 1 according to an embodiment of the present disclosure are used to incubate a culture and the cases where two other culture apparatuses 1000 are used to incubate a culture.

FIG. 15A illustrates a comparison result of the power consumption in the case where one out of two culture apparatuses is operated in the "culture mode", while the other one is operated in the "sterilization mode".

As illustrated in FIG. 15A, when using two culture apparatuses 1, the total power consumption is 1080 W (360 W+720 W), however, when using two culture apparatuses 1000, the total power consumption is 1440 W (720 W+720 W).

Further, FIG. 15B illustrates a comparison result of the power consumption when both two of them are operated in the "culture mode".

As illustrated in FIG. 15B, when using two culture apparatuses 1, the total power consumption is 720 W (360 W+360 W), however, when using two culture apparatuses 1000, the total power consumption is 1440 W (720 W+720 W).

As has been described above, according to the culture apparatus 1 of an embodiment of the present disclosure, the heaters 28 to heat the culture space 6 include the culture heater 28A and the sterilization heater 28B, and the culture heater 28A is driven without driving the sterilization heater 28B in the culture mode, while both the sterilization heater 28B and the culture heater 28A are driven in the sterilization mode, so that the power consumption in the culture apparatus 1 can be reduced.

As a result, when the culture apparatus 1 is newly provided to incubate a culture and, for example, when the upper limit on the power consumption of an electric power system of a building is 1200 W, it is possible to negate the needs for the work of reinforcing the electric power system of the building which is necessary if the other culture apparatus 1000 is introduced.

Further, even if any one of the culture apparatuses 1 is being made sterile, another culture apparatus 1 can be used, thereby being able to continually incubate a culture. With such an operation, it is possible to greatly reduce the overall power consumption of a plurality of culture apparatuses 1 when installing a plurality of culture apparatuses 1.

The above embodiments of the present disclosure are simply to facilitate understanding of the present disclosure and are not in any way to be construed as limiting the present disclosure. The present disclosure may variously be changed or altered without departing from its gist and encompass equivalents thereof.

The invention claimed is:

1. A culture apparatus comprising:
a heat-insulated casing including:
an inner case surrounding a culture space,
an outer case surrounding the inner case, and
a front surface,
the heat-insulated casing having an opening in the front surface;
a box-shaped heat-insulated door to open and close the opening of the heat-insulated casing;
heaters provided to the inner case and an inner wall of the heat-insulated door to heat the culture space; and
a control unit for controlling the heaters, wherein:
the heaters comprises first heaters and second heaters,
the first heaters are provided to rear surfaces of a top plate, a bottom plate, a back plate, and both side plates of the inner case, and a rear surface of the inner wall of the heat-insulated door, and the second heaters are provided to inner surfaces of the top plate, the bottom plate, and the back plate of the inner case, and an inner surface of the inner wall of the heat-insulated door the inner surface facing the culture space when the door is closed, but are not provided to the both side plates of the inner case, the control unit is configured to:
  turn on the first heaters and turn off the second heaters when a temperature of the culture space is controlled to, as in a culture mode, a first temperature to incubate a culture in the culture space and when a temperature of the culture space is controlled to, as in a sterilization mode, a second temperature to make the culture space sterile, the second temperature being higher than the first temperature, and
  turn on the second heaters when the temperature of the culture space is controlled to, as in the sterilization mode, the second temperature to make the culture space sterile, and the control unit is further configured to:
  once the sterilization mode is started, maintain the sterilization mode for a predetermined time period;
  turn off the first and second heaters after the predetermined time passes; and
  when the temperature in the culture space has reached a third temperature, start the culture mode, the third temperature being lower than the second temperature.

2. The culture apparatus according to claim 1, wherein: the heaters include
  a first system constituted by one or more of the first and second heaters that are provided to the rear surface of the bottom plate in the inner case,
  a second system constituted by one or more of the first and second heaters that are provided to the inner surface of the inner wall surface in the heat-insulated door,
  a third system constituted by one or more of the first and second heaters that are provided to the rear surfaces of the top plate and the back plate in the inner case, and
  a fourth system constituted by one or more of the first heaters that are provided to the rear surfaces of both the side plates in the inner case but including no second heaters, and
the control unit is configured to turn on the heaters on an individual system basis.

3. The culture apparatus according to claim 2, wherein at least one of the first heaters constituting the fourth system generates a larger amount of heat per unit time than an amount of heat generated by each of the first heaters constituting the first system to the third system.

4. The culture apparatus according to claim 1, wherein the control unit is configured to, when turning on the first heaters in the culture mode and sterilization mode, perform duty control of repeating an ON state and an OFF state to the first heaters at a predetermined cycle.

5. The culture apparatus according to claim 4, wherein the control unit is configured to, when turning on the second heaters in the sterilization mode, perform control such that the second heater is kept in an ON state.

6. The culture apparatus according to claim 1, wherein both side plates of the inner case include shelf rests formed by press working so that the shelf rests and the inner case are connected through an integral continuous surface without a boundary.

* * * * *